(12) United States Patent
Hoshen et al.

(10) Patent No.: US 9,765,334 B2
(45) Date of Patent: Sep. 19, 2017

(54) COMPOSITIONS AND METHODS FOR PROGNOSIS OF GASTRIC CANCER

(75) Inventors: Moshe Hoshen, Jerusalem (IL); Raruch Brenner, Hod Hashron (IL)

(73) Assignees: Rosetta Genomics, Ltd., Rehovot (IL); Mor Research Applications, Tel Aviv (IL)

( * ) Notice: Subject to any disclaimer, the term of this patent is extended or adjusted under 35 U.S.C. 154(b) by 689 days.

(21) Appl. No.: 12/994,411

(22) PCT Filed: May 19, 2009

(86) PCT No.: PCT/IL2009/000498
§ 371 (c)(1), (2), (4) Date: Apr. 6, 2011

(87) PCT Pub. No.: WO2009/147656
PCT Pub. Date: Dec. 10, 2009

(65) Prior Publication Data
US 2011/0177965 A1  Jul. 21, 2011

Related U.S. Application Data

(60) Provisional application No. 61/057,850, filed on Jun. 1, 2008.

(51) Int. Cl.
*C40B 30/04* (2006.01)
*C12Q 1/68* (2006.01)
*C12N 15/113* (2010.01)
*C12N 15/11* (2006.01)
*C07H 21/02* (2006.01)

(52) U.S. Cl.
CPC ........ *C12N 15/1135* (2013.01); *C12N 15/111* (2013.01); *C12Q 1/6886* (2013.01); *C12N 2310/141* (2013.01); *C12N 2320/12* (2013.01); *C12Q 2600/112* (2013.01); *C12Q 2600/118* (2013.01); *C12Q 2600/158* (2013.01); *C12Q 2600/178* (2013.01)

(58) Field of Classification Search
CPC .. C12Q 1/68; C12Q 1/6886; C12Q 2600/112; C12Q 2600/118; C12Q 2600/178; C12N 2320/12
USPC ........................................ 435/6.1, 6.11, 6.12
See application file for complete search history.

(56) References Cited

FOREIGN PATENT DOCUMENTS

WO   WO 2008048342 A2 *   4/2008   ........... C12Q 1/6837

OTHER PUBLICATIONS

Motoyama et al.; Clinical Significance of High Mobility Group A2 in Human Gastric Cancer and Its Relationship to let-7 MicroRNA Family; Clinical Cancer Research; vol. 14; pp. 2334-2340; published online Apr. 15, 2008.*
TaqMan® MicroRNA Assay; https://bioinfo.appliedbiosystems.com/genome-database/details/mirna/000377; pp. 1-2, accessed Jan. 24, 2013.*
Bandres et al.; Expression of microRNA-451 is associated with disease-free survival in gastric cancer patients treated with chemoradiotherapy after gastric resection; European Journal of Cancer Supplements; vol. 5, No. 4; pp. 90, poster 501; Sep. 2007.*
Bandres et al.; microRNA-451 RegulatesMacrophageMigration Inhibitory Factor Production and Proliferation of Gastrointestinal Cancer Cells; Human Cancer Biology; vol. 15; No. 7, pp. 2281-2290; Apr. 1, 2009.*
Hsa-mir-RG-129; Homo sapiens microRNA hsa-mir-RG-129, complete sequence; GenBank accession No. AY940875.1; published Jun. 20, 2005.*
Katada et al.; microRNA expression profile in undifferentiated gastric cancer; International Journal of Oncology; vol. 34; No. 2; pp. 537-542, Feb. 1, 2009.*

* cited by examiner

*Primary Examiner* — Antonio Galisteo Gonzalez
(74) *Attorney, Agent, or Firm* — Polsinelli PC; Ron Galant

(57) ABSTRACT

Described herein are compositions and methods for survival prediction in gastric cancer patients after surgical operation. The compositions are microRNA molecules associated with the prognosis of gastric cancer, as well as various nucleic acid molecules relating thereto or derived therefrom.

6 Claims, 12 Drawing Sheets

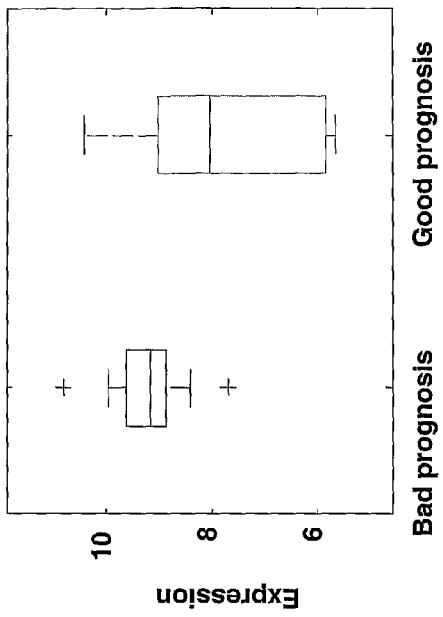
Figure 2B  hsa-miR-195
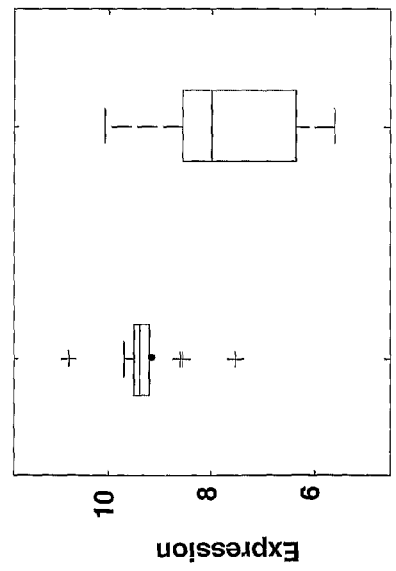
Figure 2A  hsa-miR-451
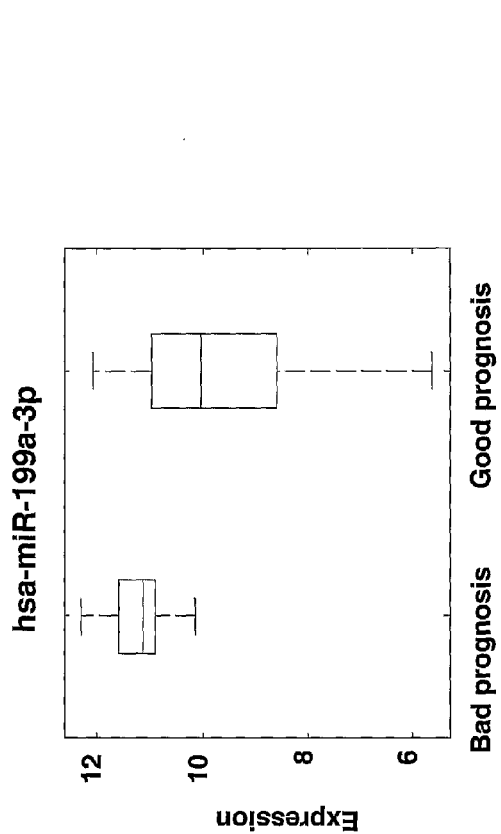
Figure 2C  hsa-miR-199a-3p

SEQUENCE LISTING

<160> NUMBER OF SEQ ID NOS: 46

<210> SEQ ID NO 1
<211> LENGTH: 22
<212> TYPE: RNA
<213> ORGANISM: human

<400> SEQUENCE: 1
aaaccguuac cauuacugag uu                                      22

<210> SEQ ID NO 2
<211> LENGTH: 21
<212> TYPE: RNA
<213> ORGANISM: human

<400> SEQUENCE: 2
uagcagcaca gaaauauugg c                                       21

<210> SEQ ID NO 3
<211> LENGTH: 22
<212> TYPE: RNA
<213> ORGANISM: human

<400> SEQUENCE: 3
acaguagucu gcacauuggu ua                                      22

```
<210> SEQ ID NO 4
<211> LENGTH: 22
<212> TYPE: RNA
<213> ORGANISM: human

<400> SEQUENCE: 4
ugagguagua guuguacag uu                                               22

<210> SEQ ID NO 5
<211> LENGTH: 22
<212> TYPE: RNA
<213> ORGANISM: human

<400> SEQUENCE: 5
ugagguagua gauuguauag uu                                              22

<210> SEQ ID NO 6
<211> LENGTH: 22
<212> TYPE: RNA
<213> ORGANISM: human

<400> SEQUENCE: 6
ugagguagua gguuguauag uu                                              22

<210> SEQ ID NO 7
<211> LENGTH: 21
<212> TYPE: RNA
<213> ORGANISM: human

<400> SEQUENCE: 7
aucacauugc caggauuuc c                                                21

<210> SEQ ID NO 8
<211> LENGTH: 23
<212> TYPE: RNA
<213> ORGANISM: human

<400> SEQUENCE: 8
cccaguguuc agacuaccug uuc                                             23

<210> SEQ ID NO 9
<211> LENGTH: 22
<212> TYPE: RNA
<213> ORGANISM: human

<400> SEQUENCE: 9
ucguaccgug aguaauaaug cg                                              22

<210> SEQ ID NO 10
<211> LENGTH: 21
<212> TYPE: RNA
<213> ORGANISM: human

<400> SEQUENCE: 10
aucacauugc caggauuac c                                                21

<210> SEQ ID NO 11
<211> LENGTH: 22
<212> TYPE: RNA
<213> ORGANISM: human

<400> SEQUENCE: 11
cagugcaaug uuaaaagggc au                                              22
```

```
<210> SEQ ID NO 12
<211> LENGTH: 21
<212> TYPE: RNA
<213> ORGANISM: human

<400> SEQUENCE: 12
uucacagugg cuaaguuccg c                                              21

<210> SEQ ID NO 13
<211> LENGTH: 21
<212> TYPE: RNA
<213> ORGANISM: human

<400> SEQUENCE: 13
uucacagugg cuaaguucug c                                              21

<210> SEQ ID NO 14
<211> LENGTH: 23
<212> TYPE: RNA
<213> ORGANISM: human

<400> SEQUENCE: 14
agcagcauug uacagggcua uga                                            23

<210> SEQ ID NO 15
<211> LENGTH: 22
<212> TYPE: RNA
<213> ORGANISM: human

<400> SEQUENCE: 15
uagcagcaca ucaugguuua ca                                             22

<210> SEQ ID NO 16
<211> LENGTH: 72
<212> TYPE: RNA
<213> ORGANISM: human

<400> SEQUENCE: 16
cuugggaaug gcaaggaaac cguuaccauu acugaguuua guaaugguaa ugguucucuu    60 gcauauaccca ga                                                       72

<210> SEQ ID NO 17
<211> LENGTH: 87
<212> TYPE: RNA
<213> ORGANISM: human

<400> SEQUENCE: 17
agcuucccug gcucuagcag cacagaaaua uuggcacagg gaagcgaguc ugccaauauu    60
ggcugugcug cuccaggcag gguggug                                        87

<210> SEQ ID NO 18
<211> LENGTH: 71
<212> TYPE: RNA
<213> ORGANISM: human

<400> SEQUENCE: 18
gccaacccag uguucagacu accguucag gaggcucuca auguguacag uagucugcac     60
auugguuagg c                                                         71

<210> SEQ ID NO 19
<211> LENGTH: 110
```

```
<212> TYPE: RNA
<213> ORGANISM: human

<400> SEQUENCE: 19
aggaagcuuc uggagauccu gcuccgucgc cccaguguuc agacuaccug uucaggacaa      60
ugccguugua caguagucug cacauugguu agacugggca agggagagca                110

<210> SEQ ID NO 20
<211> LENGTH: 84
<212> TYPE: RNA
<213> ORGANISM: human

<400> SEQUENCE: 20
aggcugaggu aguaguuugu acaguuugag ggucuaugau accacccggu acaggagaua      60
acuguacagg ccacugccuu gcca                                            84

<210> SEQ ID NO 21
<211> LENGTH: 87
<212> TYPE: RNA
<213> ORGANISM: human

<400> SEQUENCE: 21
ucagagugag guaguagauu guauaguugu gggguaguga uuuuacccug uucaggagau      60
aacuauacaa ucuauugccu ucccuga                                         87

<210> SEQ ID NO 22
<211> LENGTH: 80
<212> TYPE: RNA
<213> ORGANISM: human

<400> SEQUENCE: 22
ugggaugagg uaguagguug uauaguuuua gggucacacc caccacuggg agauaacuau      60
acaaucuacu gucuuuccua                                                 80

<210> SEQ ID NO 23
<211> LENGTH: 72
<212> TYPE: RNA
<213> ORGANISM: human

<400> SEQUENCE: 23
agguugaggu aguagguugu auaguuuaga auuacaucaa gggagauaac uguacagccu      60
ccuagcuuuc cu                                                         72

<210> SEQ ID NO 24
<211> LENGTH: 74
<212> TYPE: RNA
<213> ORGANISM: human

<400> SEQUENCE: 24
gggugaggua guagguugua uaguuugggg cucugcccug cuaugggaua acuauacaau      60
cuacugucuu uccu                                                       74

<210> SEQ ID NO 25
<211> LENGTH: 73
<212> TYPE: RNA
<213> ORGANISM: human

<400> SEQUENCE: 25
ggccggcugg gguuccuggg gaugggauuu gcuuccuguc acaaaucaca uugccaggga      60
```

```
uuuccaaccg acc                                                         73

<210> SEQ ID NO 26
<211> LENGTH: 85
<212> TYPE: RNA
<213> ORGANISM: human

<400> SEQUENCE: 26
cgcuggcgac gggacauuau uacuuuuggu acgcgcugug acacuucaaa cucguaccgu       60
gaguaauaau gcgccgucca cggca                                            85

<210> SEQ ID NO 27
<211> LENGTH: 97
<212> TYPE: RNA
<213> ORGANISM: human

<400> SEQUENCE: 27
cucaggugcu cuggcugcuu ggguuccugg caugcugauu ugugacuuaa gauuaaaauc       60
acauugccag ggauuaccac gcaaccacga ccuuggc                               97

<210> SEQ ID NO 28
<211> LENGTH: 89
<212> TYPE: RNA
<213> ORGANISM: human

<400> SEQUENCE: 28
ugcugcuggc cagagcucuu uucacauugu gcuacugucu gcaccuguca cuagcagugc       60
aauguuaaaa gggcauuggc cguguagug                                        89

<210> SEQ ID NO 29
<211> LENGTH: 78
<212> TYPE: RNA
<213> ORGANISM: human

<400> SEQUENCE: 29
cugaggagca gggcuuagcu gcuugugagc agggucacca ccaagucgug uucacagugg       60
cuaaguuccg cccccccag                                                   78

<210> SEQ ID NO 30
<211> LENGTH: 97
<212> TYPE: RNA
<213> ORGANISM: human

<400> SEQUENCE: 30
accucucuaa caaggugcag agcuuagcug auuggugaac agugauuggu uccgcuuug        60 uucacagugg cuaaguucug caccugaaga gaaggug                               97

<210> SEQ ID NO 31
<211> LENGTH: 78
<212> TYPE: RNA
<213> ORGANISM: human

<400> SEQUENCE: 31
uugugcuuuc agcuucuuua cagugcugcc uuguagcauu caggucaagc agcauuguac       60
agggcuauga aagaacca                                                    78

<210> SEQ ID NO 32
<211> LENGTH: 78
<212> TYPE: RNA
<213> ORGANISM: human
```

```
<400> SEQUENCE: 32
uacugcccuc ggcuucuuua cagugcugcc uuguugcaua uggaucaagc agcauguac    60 agggcuauga aggcauug                                                 78

<210> SEQ ID NO 33
<211> LENGTH: 98
<212> TYPE: RNA
<213> ORGANISM: human

<400> SEQUENCE: 33
uugaggccuu aaaguacugu agcagcacau cauggguuuac augcuacagu caagaugcga   60
aucauuauuu gcugcucuag aaauuuaagg aaauucau                           98

<210> SEQ ID NO 34
<211> LENGTH: 22
<212> TYPE: RNA
<213> ORGANISM: human

<400> SEQUENCE: 34
uggacuugga gucaggaggc cu                                             22

<210> SEQ ID NO 35
<211> LENGTH: 21
<212> TYPE: RNA
<213> ORGANISM: human

<400> SEQUENCE: 35
acuggacuug gagucagaag g                                              21

<210> SEQ ID NO 36
<211> LENGTH: 22
<212> TYPE: RNA
<213> ORGANISM: human

<400> SEQUENCE: 36
uauugcacuu gucccggccu gu                                             22

<210> SEQ ID NO 37
<211> LENGTH: 22
<212> TYPE: RNA
<213> ORGANISM: human

<400> SEQUENCE: 37
caugccuuga guguaggacc gu                                             22

<210> SEQ ID NO 38
<211> LENGTH: 23
<212> TYPE: RNA
<213> ORGANISM: human

<400> SEQUENCE: 38
ugagugugug ugugugagug ugu                                            23

<210> SEQ ID NO 39
<211> LENGTH: 23
<212> TYPE: RNA
<213> ORGANISM: human

<400> SEQUENCE: 39
ugaggggcag agagcgagac uuu                                            23
```

```
<210> SEQ ID NO 40
<211> LENGTH: 78
<212> TYPE: RNA
<213> ORGANISM: human

<400> SEQUENCE: 40
gagucacagu ggacuuggag ucaggaggcc ugagguccuu gaagaccucc cugaccugcu    60
cugguccacu gugugcuc                                                  78

<210> SEQ ID NO 41
<211> LENGTH: 66
<212> TYPE: RNA
<213> ORGANISM: human

<400> SEQUENCE: 41
agggcuccug acuccagguc cuguguguua ccuagaaaua gcacuggacu uggagucaga    60
aggccu                                                               66

<210> SEQ ID NO 42
<211> LENGTH: 78
<212> TYPE: RNA
<213> ORGANISM: human

<400> SEQUENCE: 42
cuuucuacac agguugggau cgguugcaau gcuguguuuc uguaugguau ugcacuuguc    60
ccggccuguu gaguuugg                                                  78

<210> SEQ ID NO 43
<211> LENGTH: 75
<212> TYPE: RNA
<213> ORGANISM: human

<400> SEQUENCE: 43
ucaucccugg gugggauuu guugcauuac uuguguucua uauaaaguau ugcacuuguc     60
ccggccugug gaaga                                                     75

<210> SEQ ID NO 44
<211> LENGTH: 91
<212> TYPE: RNA
<213> ORGANISM: human

<400> SEQUENCE: 44
cgacuugcuu ucucuccucc augccuugag uguaggaccg uuggcaucuu aauuacccuc    60
ccacacccaa ggcuugcaaa aaagcgagcc u                                   91

<210> SEQ ID NO 45
<211> LENGTH: 96
<212> TYPE: RNA
<213> ORGANISM: human

<400> SEQUENCE: 45
gggaccugcg ugggugcggg cgugugagug uguguguguc gcuccggguc   60
cacgcucaug cacacaccca cacgcccaca cucagg                              96

<210> SEQ ID NO 46
<211> LENGTH: 94
<212> TYPE: RNA
<213> ORGANISM: human

<400> SEQUENCE: 46
```

```
auaaaggaag uuaggcugag gggcagagag cgagacuuuu cuauuuucca aaagcucggu    60
cugaggcccc ucagucuugc uuccuaaccc gcgc                               94
```

COMPOSITIONS AND METHODS FOR PROGNOSIS OF GASTRIC CANCER

CROSS REFERENCE TO RELATED APPLICATIONS

The present application claims priority under 35 U.S.C. §119(e) to U.S. Provisional Application No. 61/057,850, filed Jun. 1, 2008; which is herein incorporated by reference in its entirety.

FIELD OF THE INVENTION

The present invention relates to compositions and methods for survival prediction after surgical operation of gastric cancer. Specifically the invention relates to microRNA molecules associated with the prognosis of gastric cancer, as well as various nucleic acid molecules relating thereto or derived thereof.

BACKGROUND OF THE INVENTION

In recent years, microRNAs (miRs, miRNAs) have emerged as an important novel class of regulatory RNA, which have a profound impact on a wide array of biological processes. These small (typically 17-24 nucleotides long) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. The expression of many miRs was found to be altered in numerous types of human cancer, and in some cases strong evidence has been put forward in support of the conjecture that such alterations may play a causative role in tumor progression. There are currently about 875 known human miRs.

Gastric cancer is a highly aggressive and lethal malignancy. On a global basis, this tumor represents 8.6% of the entire cancer burden and the second leading cancer cause of death; in the year 2002, over 930,000 new cases of gastric cancer were expected and nearly 700,000 people were expected to die from the disease. Surgical resection is the standard treatment of localized gastric cancer. Its results however are generally disappointing; approximately 70% of patients undergoing successful complete (R0) resection will still experience recurrence. Attempts to improve patients outcome following surgery by using adjuvant therapy have only lead to modest improvement: trials using either postoperative chemoradiation or perioperative chemotherapy have demonstrated an absolute 10-15% reduction of the risk of recurrence. Moreover, adjuvant therapy, as given in these trials, was associated with significant morbidity and even mortality.

The unsatisfying results of surgery and the limited benefit from adjuvant therapy and its toxicity, all emphasize the need for an improved selection of patients for the various treatment strategies. For example, patients with good prognosis may be spared adjuvant therapy whereas those with poor prognosis may receive such treatment or may even be offered investigational programs. However, the current ability to determine the prognosis of an individual patient is limited and is mainly based on the extent of the local tumor spread, i.e. the TNM staging. Other prognostic factors, such as the tumor's grade, vascular invasion and perineural spread, add only little to the ability to distinguish between patients with good and bad prognosis.

The determination of the gastric cancer characteristics has a potential prognostic value and can be used to design an optimal therapy. Thus characterization of the molecular biological properties of a particular tumor could lead to a more specific and efficient therapy. A therapy could be tailored according to the molecular features of the tumor to decrease the risk of recurrence of the disease.

Furthermore monitoring means a close follow up of the disease after initial therapy. Classical clinical methods are quite insensitive for the detection of the recurrence of tumors, so that the disease will reach a progressed stage before it is found. This fact reinforces the need for a more accurate prognostication method, as close monitoring cannot lead to cure of patients who did not receive the optimal primary treatment and have recurred.

There is a variety of tools to assess the primary diagnosis in tumors such as gastric tumors. Yet, due to the diversity of the molecular characteristics of tumors, the outcome of detected tumors may vary widely. For assessing prognosis and tailoring an adequate therapy further characterization of the tumors is indispensable. In many tumors prediction of the course and the treatment necessary can be assisted by testing for the level of expression of several tumor markers. Based upon this prognosis it may be possible to choose a treatment for the particular tumor to ensure the best chances for the patient along with the lowest necessary therapeutic burden. For gastric cancer the classical methods of staging and grading of the tumor afford only a restricted prognosis, so that potentially harmful therapies are applied to avoid recurrence of tumors. If the aggressiveness of tumors could be diagnosed on the basis of molecular markers, the therapy could be better suited to the needs of the individual case.

Thus, there exists a need for identification of biomarkers that can be used as prognostic indicators for gastric cancer.

SUMMARY OF THE INVENTION

According to some aspects of the present invention altered expression levels of specific nucleic acid sequences (SEQ ID NOS: 1-46) in biological samples obtained from gastric cancer patients is indicative of the cancer prognosis: the life expectancy of the patient and the risk of recurrence.

According to one aspect of the invention, a method for determining a prognosis for gastric cancer in a subject is provided, the method comprising:
 (a) obtaining a biological sample from the subject;
 (b) determining the expression level of a nucleic acid sequence selected from the group consisting of SEQ ID NOS: 1-46 and sequences at least about 80% identical thereto from said sample; and
 (c) comparing said expression level to a threshold expression level,
wherein the expression level of the nucleic acid sequence compared to said threshold expression level is indicative of the prognosis of said subject.

According to one embodiment, increased expression level of a nucleic acid sequence selected from the group consisting of SEQ ID NOS: 1-33 and sequences at least about 80% identical thereto compared to the threshold expression level is indicative of poor prognosis.

According to another embodiment, increased expression level of a nucleic acid sequence selected from the group consisting of SEQ ID NOS: 1-3 and sequences at least about 80% identical thereto compared to the threshold expression level is indicative of poor prognosis.

According to a further embodiment, decreased expression level of a nucleic acid sequence selected from the group consisting of SEQ ID NOS: 34-46 and sequences at least about 80% identical thereto compared to the threshold expression level is indicative of poor prognosis of said subject.

According to yet another embodiment, said expression level is a change in a score based on a combination of expression level of said nucleic acid sequences.

In certain embodiments, the subject is a human.

In certain embodiments, the method is used to determine a course of treatment of the subject.

In certain embodiments the biological sample obtained from the subject is selected from the group consisting of bodily fluid, a cell line and a tissue sample. In certain embodiments the tissue is a fresh, frozen, fixed, wax-embedded or formalin fixed paraffin-embedded (FFPE) tissue.

In certain embodiments said tissue is a gastric tissue. In certain embodiments said tissue is a gastric tumor tissue at a specific stage.

According to some embodiments, the expression levels are determined by a method selected from the group consisting of nucleic acid hybridization, nucleic acid amplification, and a combination thereof. According to some embodiments, the nucleic acid hybridization is performed using a solid-phase nucleic acid biochip array or in situ hybridization.

According to other embodiments, the nucleic acid amplification method is real-time PCR. According to some embodiments, the PCR method comprises forward and reverse primers. According to some embodiments, the real-time PCR method further comprises a probe.

A kit for determining the prognosis of a subject with gastric cancer is also provided. The kit may comprise a probe comprising a nucleic acid sequence that is complementary to a sequence selected from SEQ ID NO: 1-46; to a fragment thereof or to a sequence at least about 80% identical thereto.

According to some embodiments, the kit further comprises forward and reverse primers.

According to other embodiments, the kit comprises reagents for performing in situ hybridization analysis.

In some embodiments, prognostic for gastric cancer comprises providing the forecast or prediction of (prognostic for) any one or more of the following: duration of survival of a patient susceptible to or diagnosed with gastric cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. In some embodiments, duration of survival is forecast or predicted to be increased. In some embodiment, duration of survival is forecast or predicted to be decreased. In some embodiments, duration of recurrence-free survival is forecast or predicted to be increased. In some embodiment, duration of recurrence-free survival is forecast or predicted to be decreased. In some embodiments, response rate is forecast or predicted to be increased. In some embodiments, response rate is forecast or predicted to be decreased. In some embodiments, duration of response is predicted or forecast to be increased. In some embodiments, duration of response is predicted or forecast to be decreased. In some embodiments, likelihood of metastasis is predicted or forecast to be increased. In some embodiments, likelihood of metastasis is predicted or forecast to be decreased.

These and other embodiments of the present invention will become apparent in conjunction with the figures, description and claims that follow.

BRIEF DESCRIPTION OF THE DRAWINGS

FIGS. 2A-2C show box-plots of the expression levels of microRNA expression (in $\log_2$ (florescence units)) between patients of adenocarcinoma of the stomach with good prognosis (no-recurrence within 36 months of surgery) and those with bad prognosis (recurrence within 36 months). Data displayed for microRNAs 451 (SEQ ID NO: 1), 195 (SEQ ID NO: 2) and 199a-3p (SEQ ID NO: 3) which were differentially expressed. Plots show the median (horizontal line), 25 to 75 percentile (box), extent of data ("whiskers", extending up to 1.5 times the interquartile range) and outliers (crosses, values outside the range of the whiskers). P-value is for the Mann-Whitney test.

DETAILED DESCRIPTION

Figure 1:
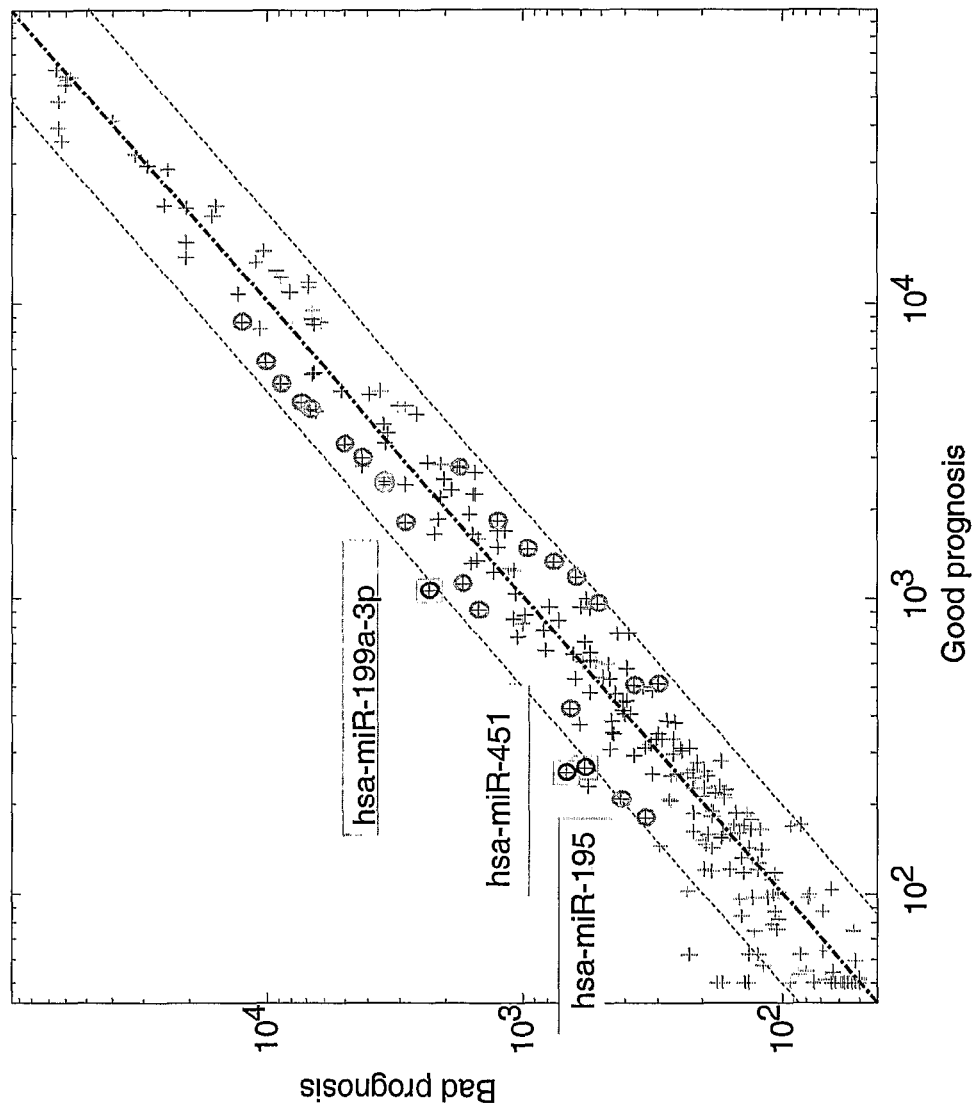
FIG. 1 demonstrates the differential expression of microRNA expression (in florescence units) between patients of adenocarcinoma of the stomach with good prognosis (no-recurrence within 36 months of surgery, n=31) and those with bad prognosis (recurrence within 36 months, n=14). microRNAs are reckoned as significantly differentially expressed if the Mann-Whitney p-value<0.024, corresponding to FDR=0.1. microRNAs are differential if additionally the fold-change between medians was >2.0. Differential microRNAs are labeled. microRNA probes were not tested if values were low in both groups or if they represent controls or spikes. The middle diagonal line represents the expected expression for non-differentially expressed miRNAs, and the other diagonal lines represent fold 2 factor lines.

According to some aspects of the present invention, miRNA expression can serve as a novel tool for the prognosis and risk of recurrence of gastric cancer. More particularly, it may serve for the prognosis of long survival versus short survival after surgical operation.

Methods and compositions are provided for the prognosis of gastric cancer. Other aspects of the invention will become apparent to the skilled artisan by the following description of the invention.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Definitions

Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Cancer Prognosis

A forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer.

Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

Differential Expression

"Differential expression" may mean qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, Northern analysis, and RNase protection.

Expression Profile

"Expression profile" as used herein may mean a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantification, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. The term "expression profile" may also mean measuring the abundance of the nucleic acid sequences in the measured samples.

Expression Ratio

"Expression ratio" as used herein refers to relative expression levels of two or more nucleic acids as determined by detecting the relative expression levels of the corresponding nucleic acids in a biological sample.

FDR

When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (such as by a two-sided t-test) below a threshold, which is dependent on the number of tests performed and the distribution of p-values obtained in these tests. FDR or false discovery rate is the probability that one of the "significant" results was actually false.

Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be a mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

Label

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Logistic Regression

Logistic regression is part of a category of statistical models called generalized linear models. Logistic regression allows one to predict a discrete outcome, such as group membership, from a set of variables that may be continuous, discrete, dichotomous, or a mix of any of these. The dependent or response variable is dichotomous, for example, one of two possible types of cancer. Logistic regression models the natural log of the odds ratio, i.e. the ratio of the probability of belonging to the first group (P) over the probability of belonging to the second group (1−P), as a linear combination of the different expression levels (in log-space) and of other explaining variables. The logistic regression output can be used as a classifier by prescribing that a case or sample will be classified into the first type if P is greater than 0.5 or 50%. Alternatively, the calculated probability P can be used as a variable in other contexts such as a 1D or 2D threshold classifier.

1D/2D Threshold Classifier

"1D/2D threshold classifier" used herein may mean an algorithm for classifying a case or sample such as a cancer sample into one of two possible types such as two types of cancer or two types of prognosis (e.g. good and bad). For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A score may be calculated as a function (usually a continuous function) of the two variables; the decision is then reached by comparing the score to the predetermined threshold, similar to the 1D threshold classifier.

Mismatch

"Mismatch" means a nucleobase of a first nucleic acid that is not capable of pairing with a nucleobase at a corresponding position of a second nucleic acid.

Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Probe

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Reference Value

As used herein the term "reference value" means a value that statistically correlates to a particular outcome when compared to an assay result. In preferred embodiments the reference value is determined from statistical analysis of studies that compare microRNA expression with known clinical outcomes. The reference value may be a threshold score value or a cutoff score value. Typically a reference value will be a threshold above which one outcome is more probable and below which an alternative threshold is more probable.

Sensitivity

"sensitivity" used herein may mean a statistical measure of how well a binary classification test correctly identifies a condition, for example how frequently it correctly classifies a cancer into the correct type out of two possible types. The sensitivity for class A is the proportion of cases that are determined to belong to class "A" by the test out of the cases that are in class "A", as determined by some absolute or gold standard.

Specificity

"Specificity" used herein may mean a statistical measure of how well a binary classification test correctly identifies a condition, for example how frequently it correctly classifies a cancer into the correct type out of two possible types. The specificity for class A is the proportion of cases that are determined to belong to class "not A" by the test out of the cases that are in class "not A", as determined by some absolute or gold standard.

Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1%

SDS, incubating at 42° C., or, 5×SSC, 1% SDS, incubating at 65° C., with wash in 0.2×SSC, and 0.1% SDS at 65° C.

Substantially Complementary

"Substantially complementary" used herein may mean that a first sequence is at least 60%-99% identical to the complement of a second sequence over a region of 8-50 or more nucleotides, or that the two sequences hybridize under stringent hybridization conditions.

Substantially Identical

"Substantially identical" used herein may mean that a first and second sequence are at least 60%-99% identical over a region of 8-50 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

Therapeutically Effective Amount

As used herein the term "therapeutically effective amount" or "therapeutically efficient" as to a drug dosage, refer to dosage that provides the specific pharmacological response for which the drug is administered in a significant number of subjects in need of such treatment. The "therapeutically effective amount" may vary according, for example, the physical condition of the patient, the age of the patient and the severity of the disease.

Treat

"Treat" or "treating" used herein when referring to protection of a subject from a condition may mean preventing, suppressing, repressing, or eliminating the condition. Preventing the condition involves administering a composition described herein to a subject prior to onset of the condition. Suppressing the condition involves administering the composition to a subject after induction of the condition but before its clinical appearance. Repressing the condition involves administering the composition to a subject after clinical appearance of the condition such that the condition is reduced or prevented from worsening. Elimination of the condition involves administering the composition to a subject after clinical appearance of the condition such that the subject no longer suffers from the condition.

Threshold Expression Level

As used herein, the phrase "threshold expression level" refers to a criterion expression profile to which measured values are compared in order to determine the prognosis of a subject with gastric cancer. The reference expression profile may be based on the expression level of the nucleic acids, or may be based on a combined metric score thereof.

Variant

"Variant" used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

b. MicroRNA and its Processing

A gene coding for a miRNA may be transcribed leading to production of a miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 30-200 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. mRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specifity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA: miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet. 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

c. Nucleic Acids

Nucleic acids are provided herein. The nucleic acid may comprise the sequence of SEQ ID NOS: 1-46 presented in table 1 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

TABLE 1

| miR_name | miR SEQ ID NO: | hairpin SEQ ID NO: | p-value | fold change | median values - Bad prognosis | median values - Good prognosis |
|---|---|---|---|---|---|---|
| Up regulated in Bad prognosis versus Good prognosis: | | | | | | |
| hsa-miR-451 | 1 | 16 | 1.70E−04 | 2.66 | 6.90E+02 | 2.60E+02 |
| hsa-miR-195 | 2 | 17 | 4.60E−03 | 2.17 | 5.80E+02 | 2.70E+02 |
| hsa-miR-199a-3p | 3 | 18, 19 | 2.70E−03 | 2.15 | 2.30E+03 | 1.10E+03 |
| hsa-let-7g | 4 | 20 | 3.50E−03 | 1.98 | 4.10E+02 | 2.10E+02 |
| hsa-let-7f | 5 | 21 | 3.60E−03 | 1.86 | 3.40E+02 | 1.80E+02 |
| hsa-let-7a | 6 | 22, 23, 24 | 2.30E−03 | 1.66 | 8.80E+03 | 5.30E+03 |
| hsa-miR-23a | 7 | 25 | 5.80E−03 | 1.61 | 1.00E+04 | 6.30E+03 |
| hsa-miR-199a-5p | 8 | 18, 19 | 1.30E−02 | 1.61 | 7.50E+03 | 4.60E+03 |
| hsa-miR-126 | 9 | 26 | 1.50E−02 | 1.61 | 1.50E+03 | 9.10E+02 |
| hsa-miR-23b | 10 | 27 | 7.50E−04 | 1.57 | 6.80E+03 | 4.40E+03 |
| hsa-miR-130a | 11 | 28 | 6.70E−03 | 1.56 | 6.60E+02 | 4.20E+02 |
| hsa-miR-27a | 12 | 29 | 2.30E−03 | 1.56 | 2.80E+03 | 1.80E+03 |
| hsa-miR-27b | 13 | 30 | 6.30E−03 | 1.52 | 1.70E+03 | 1.10E+03 |
| hsa-miR-103 | 14 | 31, 32 | 4.60E−02 | 1.51 | 6.50E+03 | 4.30E+03 |
| hsa-miR-15b | 15 | 33 | 2.80E−02 | 2.4 | 5.60E+02 | 2.30E+02 |
| Down regulated in Bad prognosis versus Good prognosis: | | | | | | |
| *MID-00689 | 34 | 40 | 2.90E−03 | 1.9 | 6.20E+02 | 1.20E+03 |
| hsa-miR-378 | 35 | 41 | 5.80E−03 | 1.86 | 5.20E+02 | 9.60E+02 |
| hsa-miR-92a | 36 | 42, 43 | 1.40E−02 | 1.73 | 7.70E+02 | 1.30E+03 |
| hsa-miR-532-5p | 37 | 44 | 9.70E−03 | 1.72 | 3.00E+02 | 5.10E+02 |
| hsa-miR-574-5p | 38 | 45 | 4.30E−03 | 1.56 | 1.80E+03 | 2.80E+03 |
| hsa-miR-423-5p | 39 | 46 | 3.70E−03 | 1.53 | 9.60E+02 | 1.50E+03 |

The microRNA name is the miRBase registry name (release 10).
*This miR is not in the miRBase registry and was cloned at Rosetta Genomics laboratory.

i. Nucleic Acid Complex

The nucleic acid may further comprise one or more of the following: a peptide, a protein, a RNA-DNA hybrid, an antibody, an antibody fragment, a Fab fragment, and an aptamer. The nucleic acid may also comprise a protamine-antibody fusion protein as described in Song et al (Nature Biotechnology 2005; 23:709-17) and Rossi (Nature Biotechnology 2005: 23; 682-4), the contents of which are incorporated herein by reference. The protamine-fusion protein may comprise the abundant and highly basic cellular protein protamine. The protamine may readily interact with the nucleic acid. The protamine may comprise the entire 51 amino acid protamine peptide or a fragment thereof. The protamine may be covalently attached to another protein, which may be a Fab. The Fab may bind to a receptor expressed on a cell surface.

ii. Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-46 or variants thereof.

The pri-miRNA may form a hairpin structure. The hairpin may comprise first and second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

iii. Pre-miRNA

The nucleic acid may also comprise a sequence of a pre-miRNA or a variant thereof. The pre-miRNA sequence may comprise from 45-200, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-46 or variants thereof.

iv. mRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-15 and 34-39 or variants thereof.

v. Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-15 and 34-39, or variants thereof.

vi. Binding Site of Target

The nucleic acid may also comprise a sequence of a target miRNA binding site, or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 nucleotides of the complementarity sequence of SEQ ID NOS: 1-15 and 34-39.

d. Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

e. Probes

A probe is also provided comprising a nucleic acid described herein. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

f. Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

g. Diagnosis

A method of diagnosis is also provided. The method comprises detecting a differential expression level of gastric cancer-associated nucleic acid in a biological sample. The sample may be derived from a patient. Diagnosis of a disease state in a patient may allow for prognosis and selection of therapeutic strategy. Furthermore, the developmental stage of cells may be classified by determining temporarily expressed gastric cancer-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the nucleic acids which indicate the diagnosis may differ from those which indicate the prognosis and molecular profiling of the condition of the cells may lead to distinctions between responsive or refractory conditions or may be predictive of outcomes.

e. Biomarkers

Biomarkers are also provided. One type of cancer screening test involves the detection of a biomarker, such as a tumor marker, in a fluid or tissue obtained from a patient. Tumor markers are substances produced by cancer cells that are not typically produced by normal cells. These substances generally can be detected in the body fluids or tissues of patients with cancer. Another important use for tumor markers is for monitoring patients being treated for advanced cancer. Measuring tumor markers for this purpose can be less invasive, less time-consuming, as well as less expensive, than other complicated tests, to determine if a therapy is reducing the cancer.

A further important use for tumor markers is for determining a prognosis of survival of a cancer patient. Such prognostic methods can be used to identify surgically treated patients likely to experience cancer recurrence so that they can be offered additional therapeutic options. Biomarkers useful for prognosis of survival also can be especially effective for determining the risk of metastasis in patients who demonstrate no measurable metastasis at the time of examination or surgery. Knowledge of the likelihood of metastasis in a cancer patient can be an important factor in selecting a treatment option. For example, a cancer patient likely to experience metastasis may be advantageously treated using a modality that is particularly aggressive.

f. Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be a kit for the amplification, detection, identification or quantification of a target nucleic acid sequence. The kit may comprise a poly(T) primer, a forward primer, a reverse primer, and a probe.

Having now generally described the invention, the same will be more readily understood through reference to the following examples, which are provided by way of illustration and are not intended to be limiting of the present invention.

EXAMPLES

Materials and Methods

Patients

The study population consisted of patients with histologically confirmed adenocarcinoma of the stomach that were operated and followed at the Rabin Medical Center (RMC), Petach Tikva, Israel. Patients with cardiac tumors extending into the gastroesophageal junction (GEJ) were eligible but those with predominantly esophageal or GEJ tumors (Siewert classification I-II) were excluded. All patients underwent potentially curative gastrectomies with clear margins (R0 resection) and had no evidence of distant spread. For purposes of the quality of the surgical specimens on one hand and adequate length of follow-up on the other hand, eligible patients had to be operated between 1995 and 2005. To isolate a prognostic from a predictive effect, patients who received any pre- or postoperative adjuvant therapy were excluded. In order to evaluate the patients three year disease-free survival (DFS), a minimum follow-up of three years for non-recurring patients was mandatory. Eligible patients, fulfilling all these criteria, were identified from the database of the Institute of Oncology at the RMC, following the study approval by the local ethics committee.

Follow-Up

In accordance with the retrospective nature of the study, the follow-up policy was determined by the treating physician; still, all patients were followed every three to six months in the first three years, regardless of the stage of their disease. Follow-up visits consisted of a medical history, physical examination and testing of the carcinoembryonic antigen (CEA) serum level. The study group was divided into those who did ("recurrent") and those who did not ("non-recurrent") experience recurrence of disease within the first three years of follow-up.

Pathology

Paraffin embedded blocks of the surgical specimens from the initial gastrectomies of the eligible patients were and retrieved from the archive of the Institute of Pathology at the RMC. Only blocks containing above 50% tumor and larger than 0.5 cm in diameter were considered suitable for this research. Each block was sampled by 10×10μ slices, kept in one eppendorf for purposes of microRNA analysis. In addition, a 4μ slide dyed with Hematoxyllin and Eusin (H&E) was prepared from each block. All H&E slides were reviewed by two expert pathologists (TD, MH), who confirmed the diagnosis and the appropriate percentage of tumor in the specimen as well as other parameters, such as the tumor histological type, grade and presence of invasive features (eg. perineural invasion).

RNA Extraction

Total RNA was isolated from seven to ten 10-μm-thick FFPE tissue sections using the miRdicator™ extraction protocol developed at Rosetta Genomics. Briefly, the sample was incubated a few times in Xylene at 57° to remove paraffin excess, followed by Ethanol washes. Protein degradation was performed by incubation of the sample in a proteinase K solution at 45° C. for a few hours. The RNA was extracted using acid phenol/chloroform followed by ethanol precipitation and DNAse digestion. Total RNA quantity and quality was measured by spectrophotometer (Nanodrop ND-1000, Nanoprop Technologies, Wilmington, Del.).

miR Array Platform

Custom microRNA microarrays were produced by printing DNA oligonucleotide probes representing ~900 DNA oligonucleotide probes representing microRNAs (Sanger database version 10 and additional microRNAs predicted and validated by Rosetta Genomics). Each probe, spotted in triplicate, carries up to 22-nt linker at the 3' end of the microRNA's complement sequence in addition to an amine group used to couple the probes to coated glass slides. 20 μM of each probe were dissolved in 2×SSC+0.0035% SDS and spotted in triplicate on Schott Nexterion® Slide E coated microarray slides using a Genomic Solutions® BioRobotics MicroGrid II according the MicroGrid manufacturer's directions. 54 negative control probes were designed using the sense sequences of different microRNAs. Two groups of positive control probes were designed to hybridize to miR array (i) synthetic small RNAs were spiked into each RNA sample before labeling to verify labeling efficiency and (ii) probes for abundant small RNAs (e.g. small nuclear RNAs (U43, U49, U24, Z30, U6, U48, U44), 5.8s and 5s ribosomal RNA) were spotted on the array to validate RNA quality. The slides were blocked in a solution containing 50 mM ethanolamine, 1M Tris (pH9.0) and 0.1% SDS for 20 min at 50° C., then thoroughly rinsed with water and spun dry.

Cy-Dye Labeling of MicroRNA for MiRdicator™ Array

Five μg of total RNA were labeled by ligation (Thomson et al., Nature Methods 2004, 1:47-53) of an RNA-linker, p-rCrU-Cy/dye (Dharmacon), to the 3'-end with Cy3 or Cy5. The labeling reaction contained total RNA, spikes (0.1-20 fmoles), 300 ng RNA-linker-dye, 15% DMSO, 1× ligase buffer and 20 units of T4 RNA ligase (NEB) and proceeded at 4° C. for 1 hr followed by 1 hr at 37° C. The labeled RNA was mixed with 3× hybridization buffer (Ambion), heated to 95° C. for 3 min and then added on top of the miRdicator™ array. Slides were hybridized 12-16 hr in 42° C., followed by two washes in room temperature with 1×SSC and 0.2% SDS and a final wash with 0.1×SSC.

Arrays were scanned using an Agilent Microarray Scanner Bundle G2565BA (resolution of 10 μm at 100% power). Array images were analyzed using SpotReader software (Niles Scientific).

Signal Calculation and Normalization

The RNA fluorescence data from the slide corresponding to each patient was loaded into a single database. Microarray spots were combined and signals were normalized. Data was log-transformed and subsequent analysis was performed in log-space. Henceforth, the expression level or signal of an individual microRNA (henceforth: miR) refers to the normalized value. The miR profile of each patient was visually compared with the median value for all patients. 11 samples for which the readings were clearly incomparable (i.e., overall pattern too noisy) were excluded. These samples did not differ in their survival patterns from the 45 samples which were kept for statistical analysis (p=0.28 by logrank). Only samples which passed this analysis were included in further analysis.

Data Analysis and Statistics

Eligible patients for this study were those patients who fulfilled all the clinical eligibility criteria and whose surgical specimens were deemed suitable for the tissue analysis (see above). The clinical and pathological data of these patients were entered into an electronic database created for this purpose and anonymized. The microRNA measurement was performed by people who were blinded to the patients' clinical data.

The data was split by prognosis grouping into patients with or without recurrence. 111 miRs had a signal that passed the minimal threshold of 300 in at least one group. For each of these, the distributions of readings in the two groups were compared using the Wilcoxon-Mann-Whitney two-sample rank-sum test. The fold-change between the two groups, which is the ratio of the median expression levels, was calculated for each miR. miRs were deemed differential if the fold-change between groups was at least 2.0. While, in principle, a threshold of p=0.05 is pre-determined for significance, each miR is a hypothesis, and as there were 111 miRs tested there is a need to make a multiple-hypothesis correction. We treated this point in two ways. The first was by the Benjamin-Hochberg false-discovery rate (FDR), which attributes each miR to its rank among all miRs and tests whether the p-value of the miR is less than its quantile in the population multiplied by the pre-set FDR fraction, here taken as 0.1. miRs whose p-values are below this value have a probability not greater than FDR of not being truly significant. An alternative method is randomly reshuffling miR profiles between patients. Thus, each patient will receive an entire miR profile of a different patient. The p-values for each of the miRs are now recalculated and the p-value of the most significant miR under this random distribution is calculated. This process is repeated many times (typically $N_{repeat}=100$). The minimal p-values received are now ranked, and the placement of the true p-value within this list ($rank_{true}$) is obtained. $rank_{true}/N_{repeat}$ is the corrected p-value. The re-sampling method is used for evaluation of conclusions of complex analyses, such as combinations of miRs or predictive values.

For each of the leading miRs, the cohort was initially split into two groups with expression above or below the median expression of this miR. Kaplan Meier (KM) survival curves were then used to compare the two groups obtained by this division and to establish survival patterns associated with each such miR. The relevant p-value was determined by using the logrank test on the survival data for the two groups, obtained by this division for each miR. In addition the predictive power of a microRNA was maximized by finding the threshold level of the miR expression signal that provided the best separation into good vs. bad prognosis. This threshold was then used for creating new KM curves.

Stepwise Cox regression was used for combining survival patterns for different predictors (combination of miRs and combination of clinical and demographic features) in a multivariate analysis. The inclusion criterion is p<0.05 and the exclusion p>0.1. Using the coefficients of the Cox fit we created a composite score for each patient, which may serve as a prognosticator. Once again, we then found the best separation threshold achievable by this score between good and bad prognosis and performed KM analysis.

The overall goal of this study was to predict reliably non-recurrence after surgery, that is to achieve a high positive predictive value (PPV, number of correctly predicted non-recurrent patients/all patients predicted to not recur). After choosing the most relevant miR, the predictive value of the miR was optimized by finding successive miR value thresholds which maximize PPV while allowing high sensitivity of detection of non-recurrence. KM was repeated based on this separation, and logrank was repeated to measure separation.

Example 1

Clinical Predictors of Outcome

A total of 69 patients who fulfilled all the eligibility criteria and for whom paraffin blocks were available, were identified retrospectively from the database of the Institute of Oncology at the Rabin Medical Center (RMC). Fifty-six of the samples had a tumor content of at least 50%. For 45 of these samples (80.3%), a reliable microRNA expression data was obtained by microarray. Of the 45 patients included in the analysis, 14 patients (31%) experienced recurrence of disease within three years of follow-up (bad prognosis) and 31 (69%) did not (good prognosis). The patients' clinicopathological characteristics are summarized in Table 2. A comparison of the patients' clinical variables and the tumor pathological features between the two groups found that TNM stage, surgery type and location of the tumor correlated significantly with bad prognosis while age, gender, ethnicity, grade, histology and preoperative CEA levels did not.

TABLE 2

Clinicopathological characteristics

|  | All patients (n = 45) | Good prognosis (n = 31) | Bad prognosis (n = 14) | p-value[1] |
|---|---|---|---|---|
| Age (yrs) | 75 | 75.5 | 74 | 0.36 |
| Median (range) | 47-88 | 47-88 | 57-86 |  |
| Gender |  |  |  | 0.31 |
| Male | 29 (64%) | 18 (58%) | 11 (79%) |  |
| Female | 16 (36%) | 13 (42%) | 3 (21%) |  |
| Ethnicity |  |  |  | 0.46 |
| Ashkenazi | 34 (76%) | 22 (71%) | 12 (86%) |  |
| Sepharadic | 11 (24%) | 9 (29%) | 2 (14%) |  |
| Surgery type |  |  |  | 0.3 |
| Partial gastrectomy | 21 (47%) | 18 (58%) | 3 (21%) |  |
| Sub total gastrectomy | 6 (13%) | 4 (13%) | 2 (14%) |  |
| Total gastrectomy | 8 (18%) | 4 (13%) | 4 (29%) |  |
| Esophagogastrectomy | 10 (22%) | 5 (16%) | 5 (36%) |  |
| Location |  |  |  | 0.14 |
| Proximal | 19 (42%) | 12 (39%) | 7 (50%) |  |
| Distal | 20 (44%) | 17 (55%) | 3 (21%) |  |
| Diffuse | 6 (13%) | 2 (6%) | 4 (29%) |  |
| T Stage |  |  |  | 0.089 |
| T1 | 6 (13%) | 6 (23%) | 0 (0%) |  |
| T2 | 13 (29%) | 12 (37%) | 1 (7%) |  |
| T3 | 25 (56%) | 13 (40%) | 12 (86%) |  |
| T4 | 1 (2%) | 0 (0%) | 1 (7%) |  |
| N Stage |  |  |  | 0.12 |
| N0 | 28 (62%) | 23 (74%) | 5 (36%) |  |
| N1 | 13 (29%) | 7 (23%) | 6 (43%) |  |
| N2 | 4 (9%) | 1 (3%) | 3 (21%) |  |
| TNM Stage |  |  |  | 0.036 |
| 1 | 15 (34%) | 14 (45%) | 1 (8%) |  |
| 2 | 15 (34%) | 11 (35%) | 4 (31%) |  |
| 3 | 14 (32%) | 6 (19%) | 8 (62%) |  |
| Grade |  |  |  | 0.6 |
| I | 4 (9%) | 4 (13%) | 0 (0%) |  |
| II | 21 (47%) | 15 (48%) | 6 (43%) |  |
| III | 20 (44%) | 12 (39%) | 8 (57%) |  |
| Examined LN |  |  |  | 0.89 |
| ≤10 | 19 (42%) | 13 (42%) | 6 (43%) |  |
| >10 | 26 (58%) | 18 (58%) | 7 (57%) |  |
| Histology[2] |  |  |  | 0.6 |
| Intestinal | 12 (75%) | 10 (77%) | 2 (67%) |  |
| Diffuse | 4 (25%) | 3 (23%) | 1 (33%) |  |
| Mucin secretion |  |  |  | 1 |
| Yes | 6 (13%) | 4 (13%) | 2 (14%) |  |
| No | 39 (87%) | 27 (87%) | 12 (86%) |  |
| Signet |  |  |  | 1 |
| Yes | 6 (13%) | 4 (13%) | 2 (14%) |  |
| No | 39 (87%) | 26 (87%) | 12 (86%) |  |
| Vascular invasion |  |  |  | 0.085 |
| Yes | 8 (18%) | 3 (10%) | 5 (36%) |  |
| No | 37 (82%) | 28 (90%) | 9 (64%) |  |
| Perineural invasion |  |  |  | 0.64 |
| Yes | 5 (11%) | 3 (10%) | 2 (14%) |  |
| No | 40 (89%) | 28 (90%) | 12 (86%) |  |
| Site of reccurence |  |  |  | $1.4\ 10^{-5}$ |
| Locoregional | 3 (6%) | 0 (0%) | 3 (21%) |  |
| Distant | 8 (1718%) | 1 (3%) | 7 (50%) |  |
| Combined | 7 (16%) | 3 (10%) | 4 (29%) |  |

Abbreviations:
LN = lymph nodes;
[1]P-value of the comparison between the patients with bad and good prognosis.
[2]Data on histology was missing in 30 patients.

Example 2

Specific MicroRNAs are Able to Predict the Prognosis of Gastric Cancer

The statistical analysis of the miR arrays results and comparison of the median values of miR expression in tumor samples obtained from gastric cancer patients with poor (bad) prognosis, with the median values of miR expression in tumor samples obtained from patients with good prognosis, revealed a significant difference in the expression pattern of specific miRs as specified in Table 1. The normalized expression levels of several miRs, e.g., hsa-miR-451 (SEQ ID NO: 1), were found to increase while the normalized expression levels of several miRs, e.g., MID 00689 (SEQ ID NO: 34) were found to decrease in patients with poor prognosis. Accordingly, up regulation of hsa-miR-451 and down regulation of MID 00689 is demonstrated to be predictive of poor prognosis.

Example 3

Molecular Predictors

Figure 3:
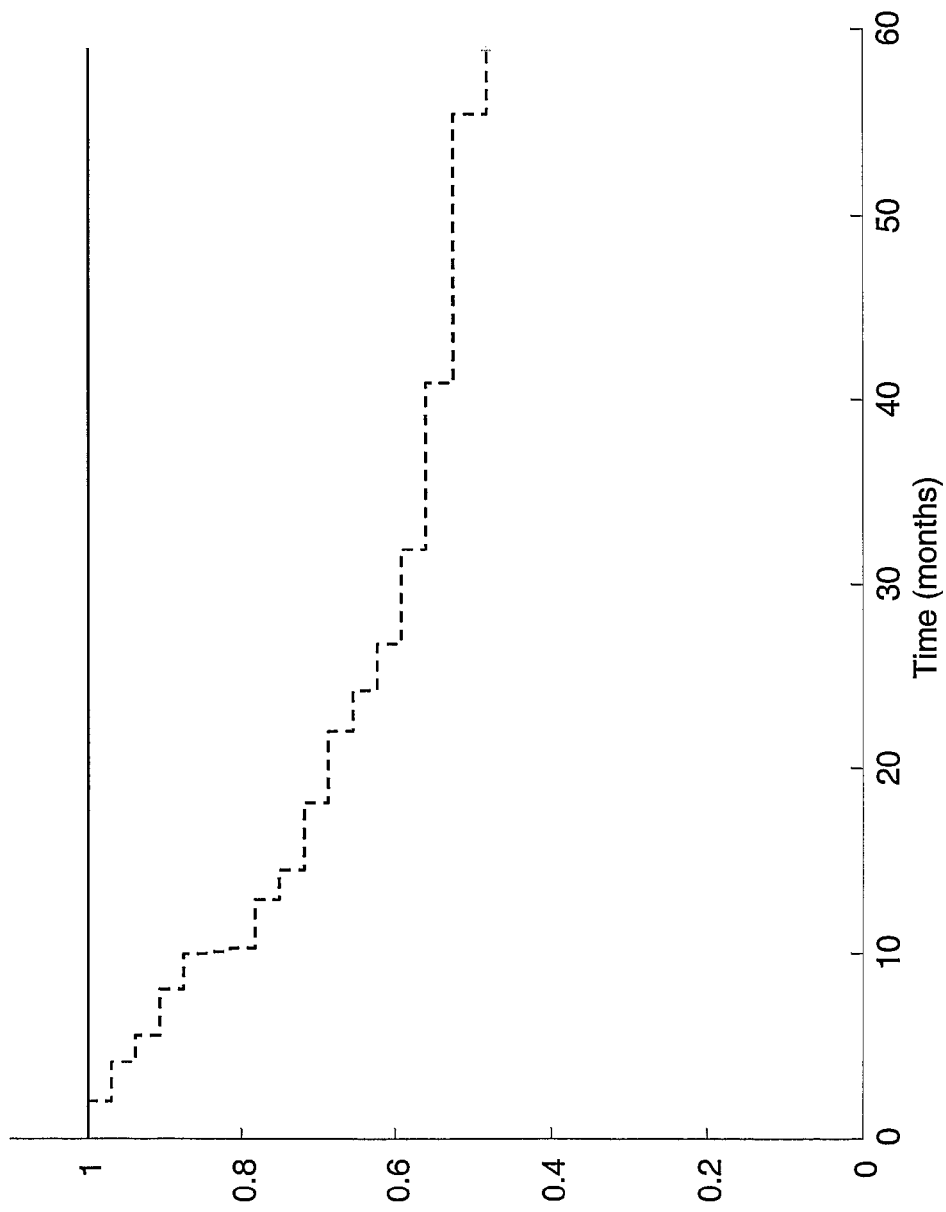
FIG. 3 is a Kaplan-Meier model of recurrence for gastric cancer patients. Fraction remaining non-recurrent as function of time from surgery. Population split by hsa-miR-451 (SEQ ID NO: 1) expression (in $\log_2$(florescence units)), based on best separation. P-value (0.00093) calculated by logrank. Solid line—n=13 (≤7.5), dashed line—n=32 (>7.5).
Figure 4A:
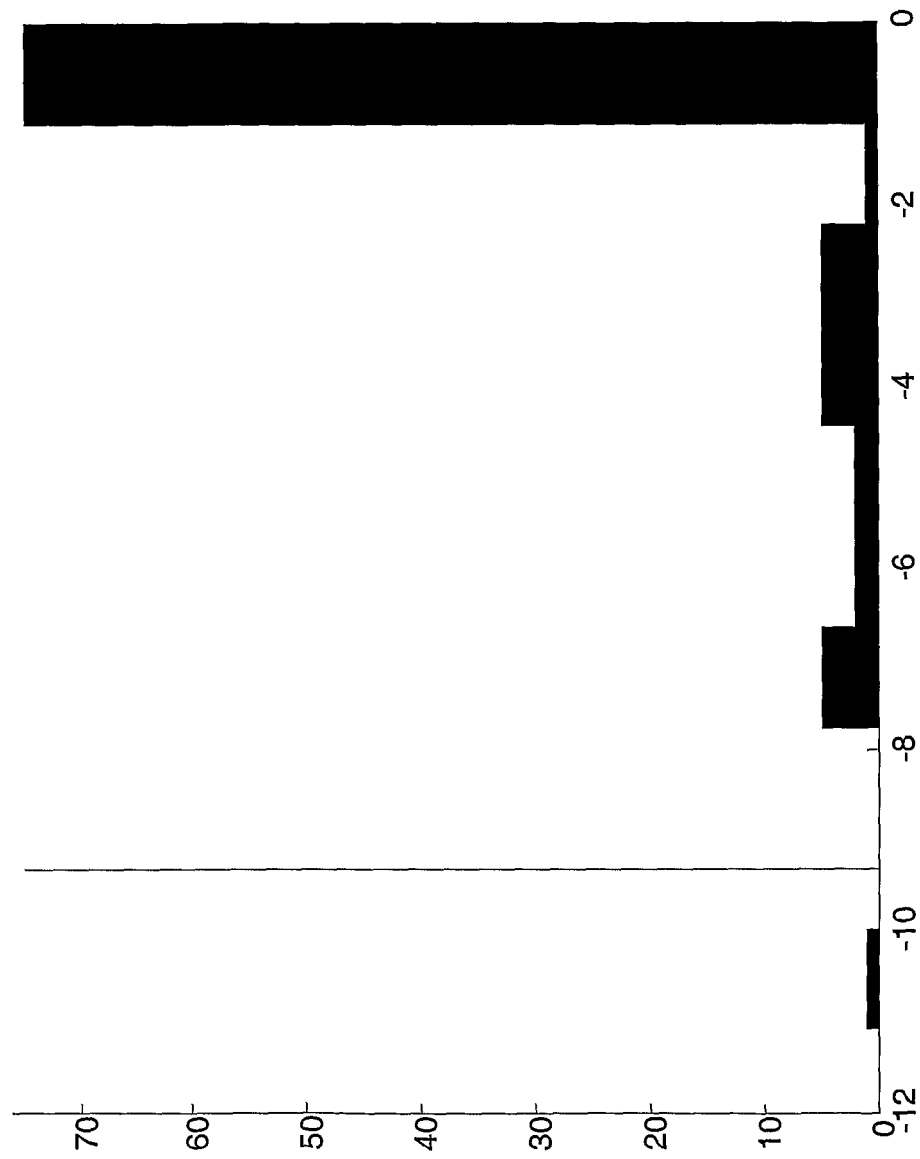
FIGS. 4A-4B are histograms of $\log_{10}$ (p-value) calculated for the best microRNA for a randomly relabeled population. Results presented are from 100 such relabellings. P reported is the relative rank of the true p-value among that received for random models. Vertical line represents the true value. (a). single microRNA model. Corrected P (by randomization) of the 1-miR model is 0.01. (b) two-microRNA model. Corrected P (by randomization) of the 2-miR model is 0.01.
Figure 4B:
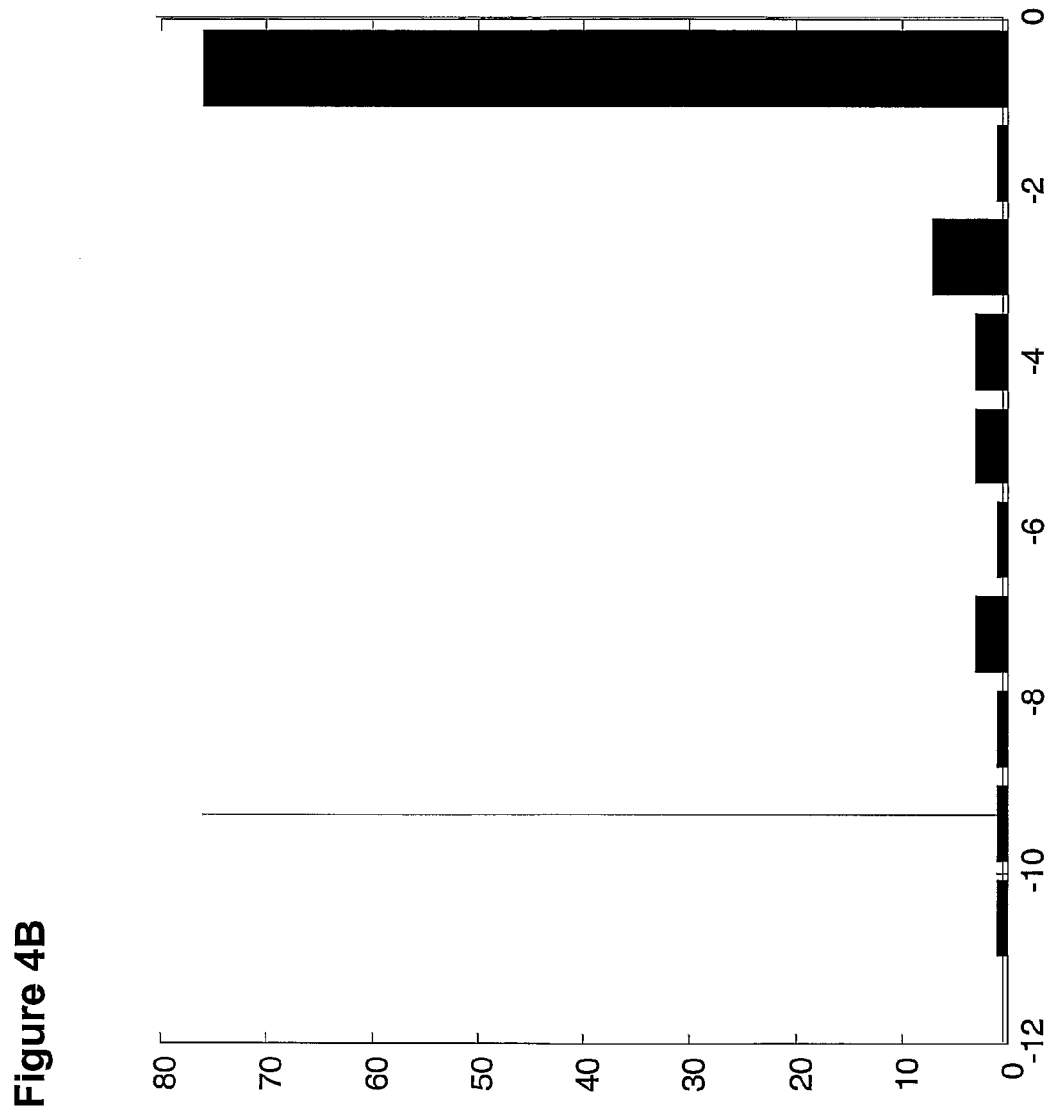
Figure 5A:
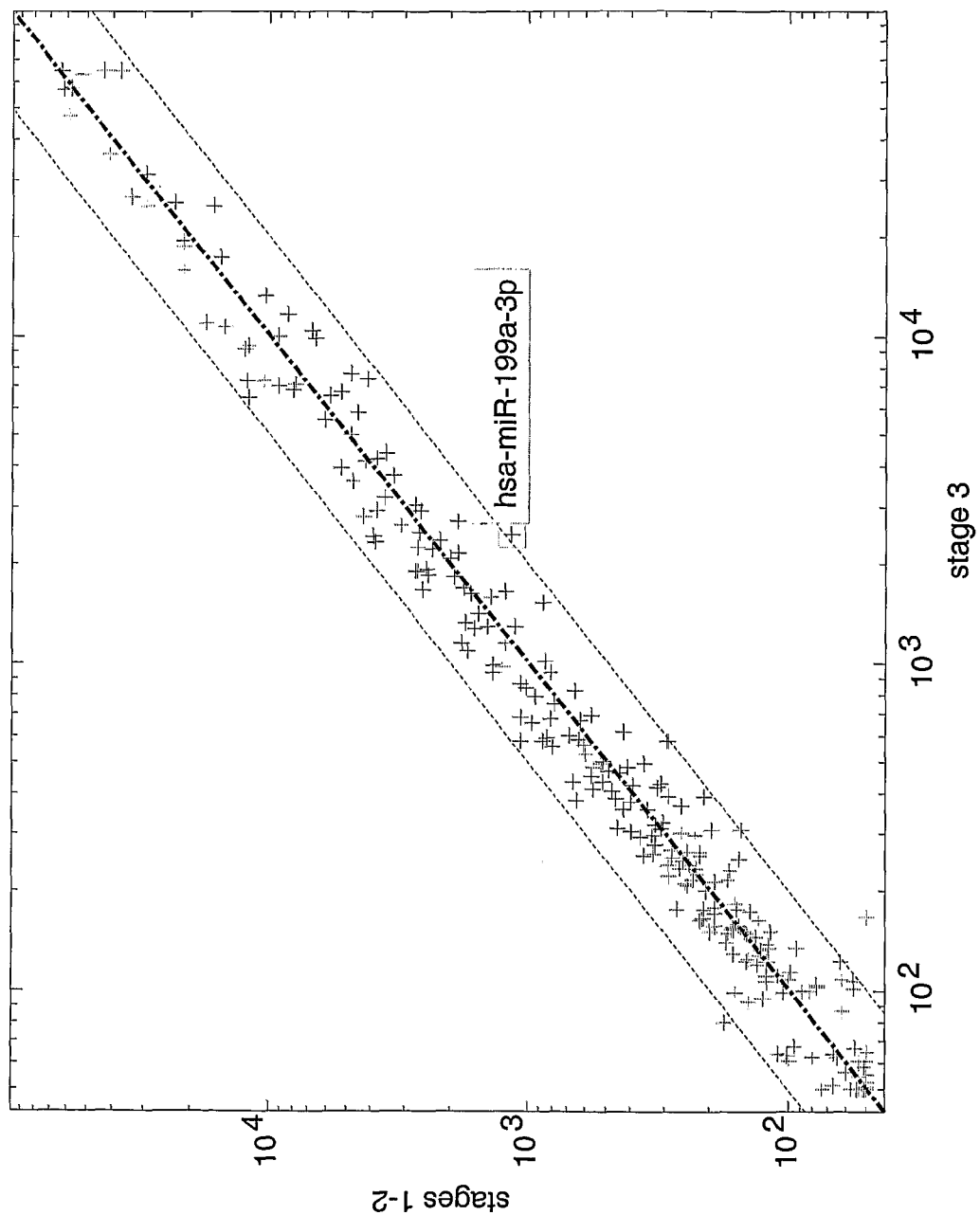
FIGS. 5A-5C demonstrate the differential expression of microRNA expression (in florescence units) between patients of adenocarcinoma of the stomach at different stages. microRNAs are reckoned as differentially expressed if the fold-change between medians was >2.0. Differentially expressed microRNAs are labeled. microRNA probes were not tested if values were low in both groups or if they represent controls or spikes. (a) combined stages 1 and 2 (n=30) versus stage 3 (n=14). (b) stage 1 (n=15) versus combined stages 2 and 3 (n=29). (c) stage 2 (n=15) versus stage 3 (n=14).
Figure 5B:
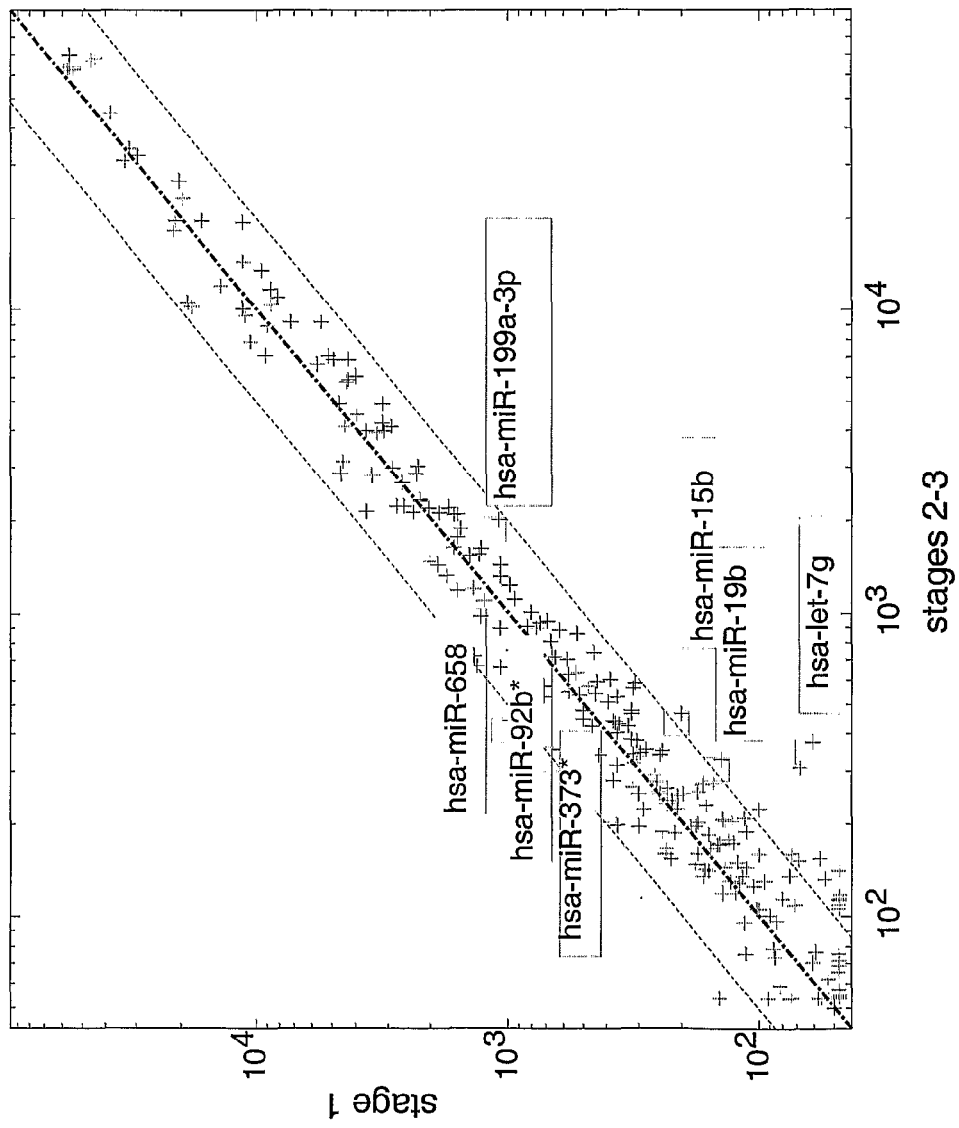
Figure 5C:
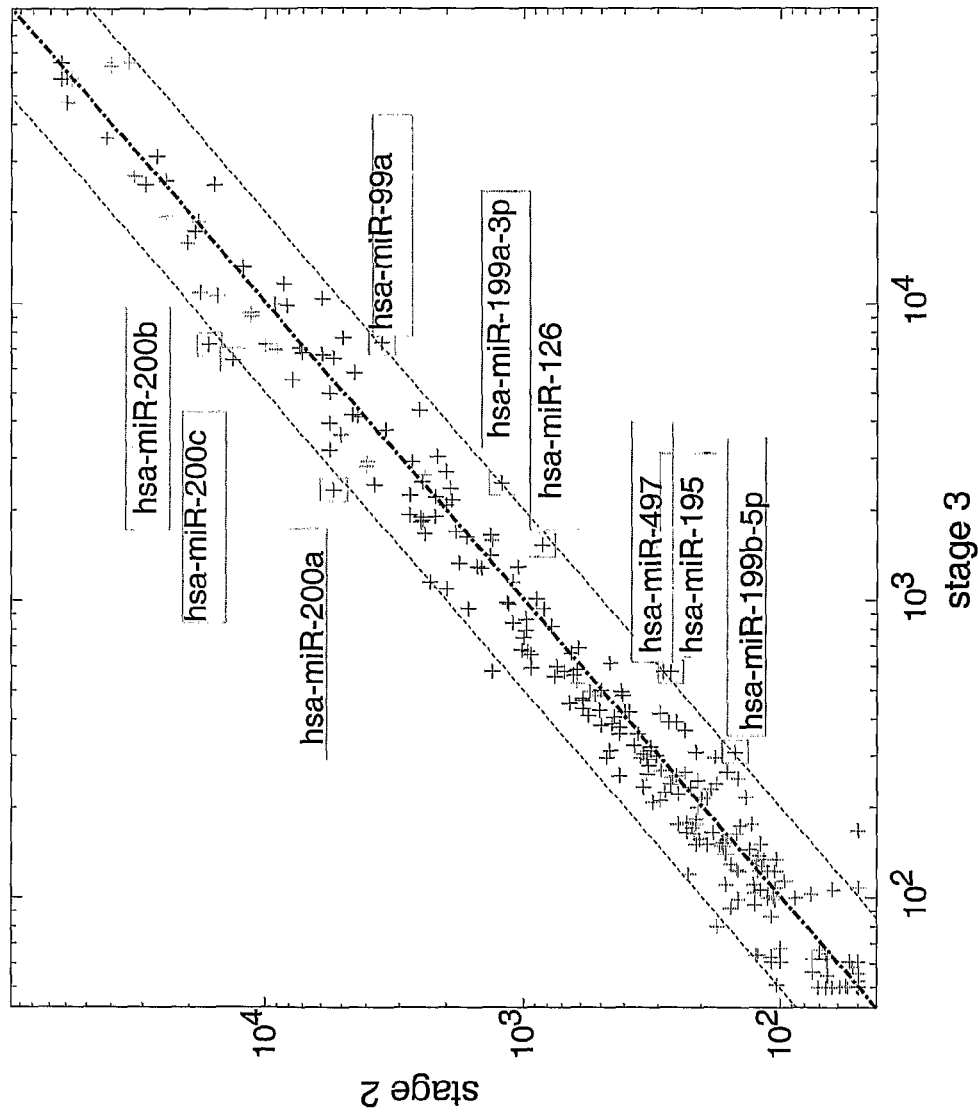
Figure 6:
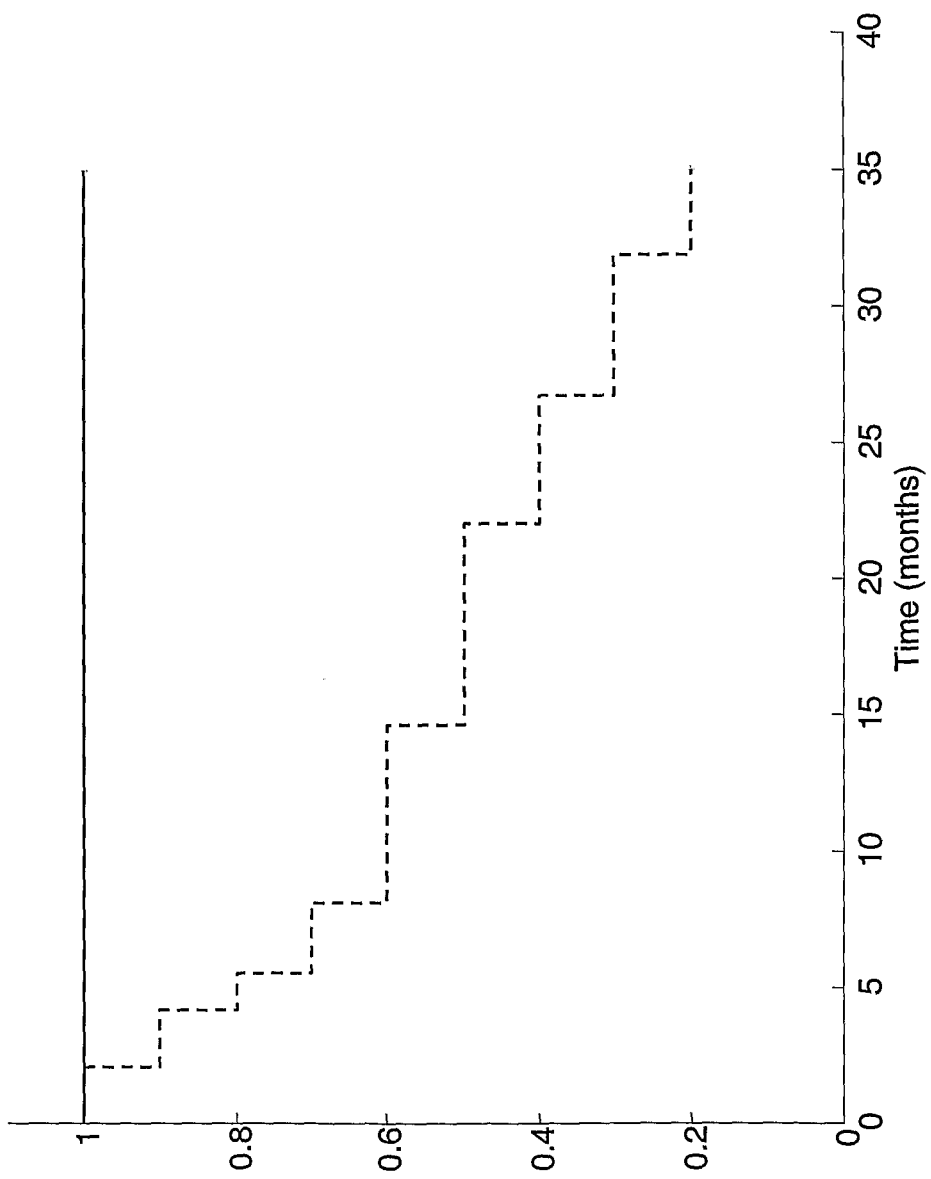
FIG. 6 is a Kaplan-Meier model of recurrence for gastric cancer patients at stage 3. Fraction remaining non-recurrent as function of time from surgery. Population split by hsa-miR-451 (SEQ ID NO: 1) expression (in $\log_2$(florescence units)), based on best separation. P-value (0.015) calculated by logrank. Solid line—n=4 (≤0.075), dashed line—n=10 (>0.075).

One miR, hsa-miR-451 (SEQ ID NO: 1), had a fold change greater than 2.0 with p<0.001. However, two other miRs, hsa-miR-199a-3p (SEQ ID NO: 3), and hsa-miR-195 (SEQ ID NO: 2) also passed FDR=0.1 with a fold change>2 (FIG. 1). The boxplots of the separation of the miR expression for good and bad prognosis is presented in FIG. 2. hsa-miR-451 was an excellent prognosticator of recurrence-free survival allowing the identification of a group (n=13 without a single case of recurrence within three years (FIG. 3). Out of 100 repeats of random re-assignment of miR patterns and forming of KM survival curves recreated, only one instances generated a logrank p-value lower than the separation for hsa-miR-451 (hence an adjusted p=0.01, FIG. 4a). Correlation between the differential miRs was fair (r~0.6), except for between hsa-miR-199a-3p and hsa-miR-195 (r=0.86), suggesting that they are independent predictors, and that linear combination of the miRs may increase their predictive value. Indeed, using logistic regression, a combination of hsa-miR-451 (SEQ ID NO: 1) and hsa-miR-199a-3p (SEQ ID NO: 3) produced an excellent separation (FIG. 4b). In only one case in 100 was a combination of two miRs in a randomized re-assignment of miRs a better predictor of prognosis. The miRs were not related to the most typical predictor of prognosis, stage, as they were not differentially expressed between stage 1 and stages 2-3 (FIG. 5B), stages 2 and 3 (FIG. 5C) nor between stages 1-2 and stage 3 (FIG. 5A), with hsa-miR-199a-3p showing some not-significant up-regulation in stage 3. Moreover, subdividing the patient population by stage, among patients with stage 3 alone, hsa-miR-451 is an excellent predictor of poor prognosis using KM (FIG. 6). In stages 1 and 2 alone the result is not significant, due to lack of statistical power (only 1 case of recurrence in stage 1 and 4 in stage 2).

Example 4

Combining Clinical and Molecular Markers

Figure 7:
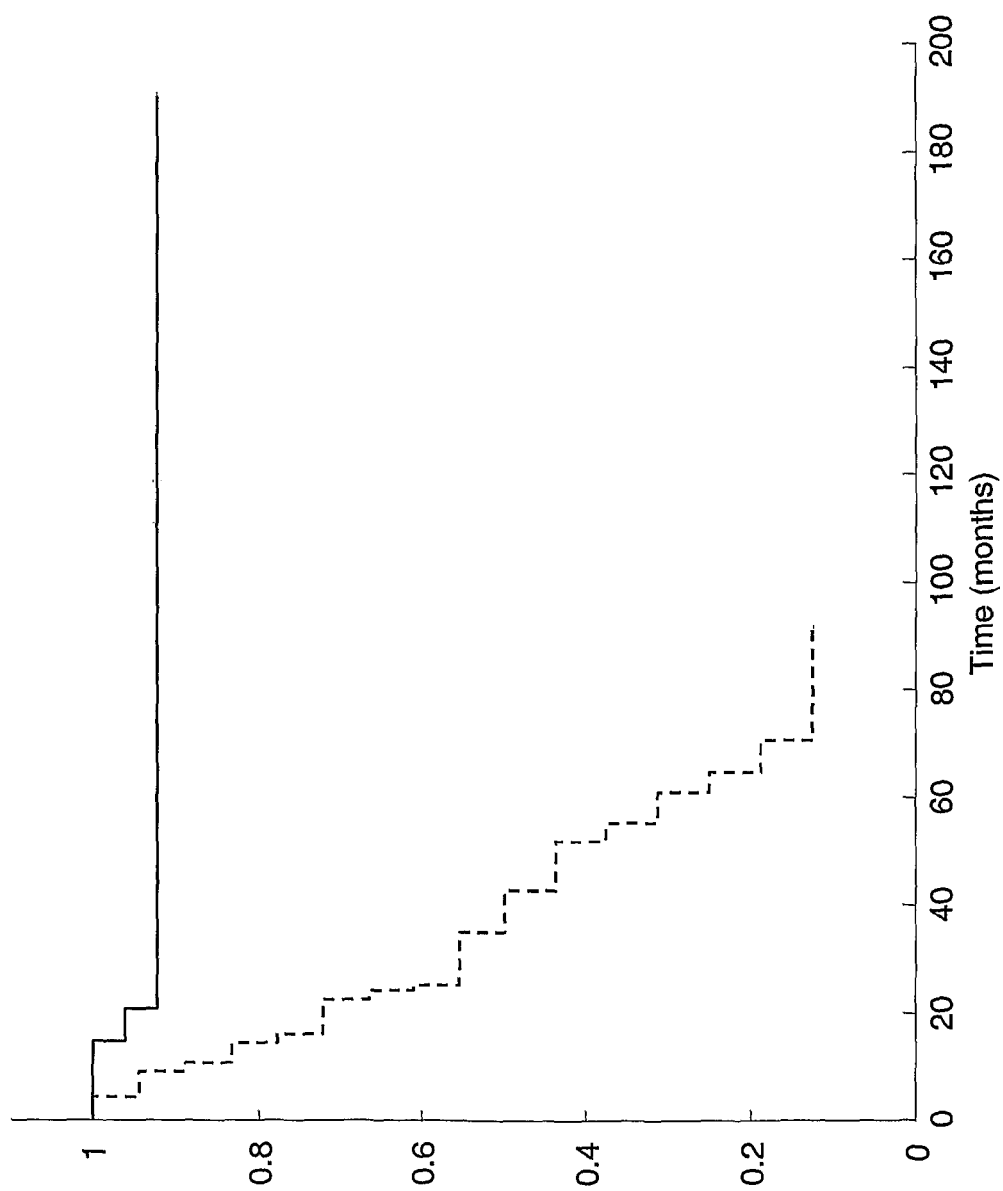
FIG. 7 is a Kaplan-Meier model of fractional survival for gastric cancer patients by time in months from surgery based on composite score based on 0.683*log$_2$(hsa-miR-451 expression), and 1.60*stage. Combination based on Cox regression coefficients. Threshold maximizes separation. P-value (2e-007) calculated by logrank. Solid line—n=26 (≤9.0783), dashed line—n=18 (>9.0783).
Figure 8:
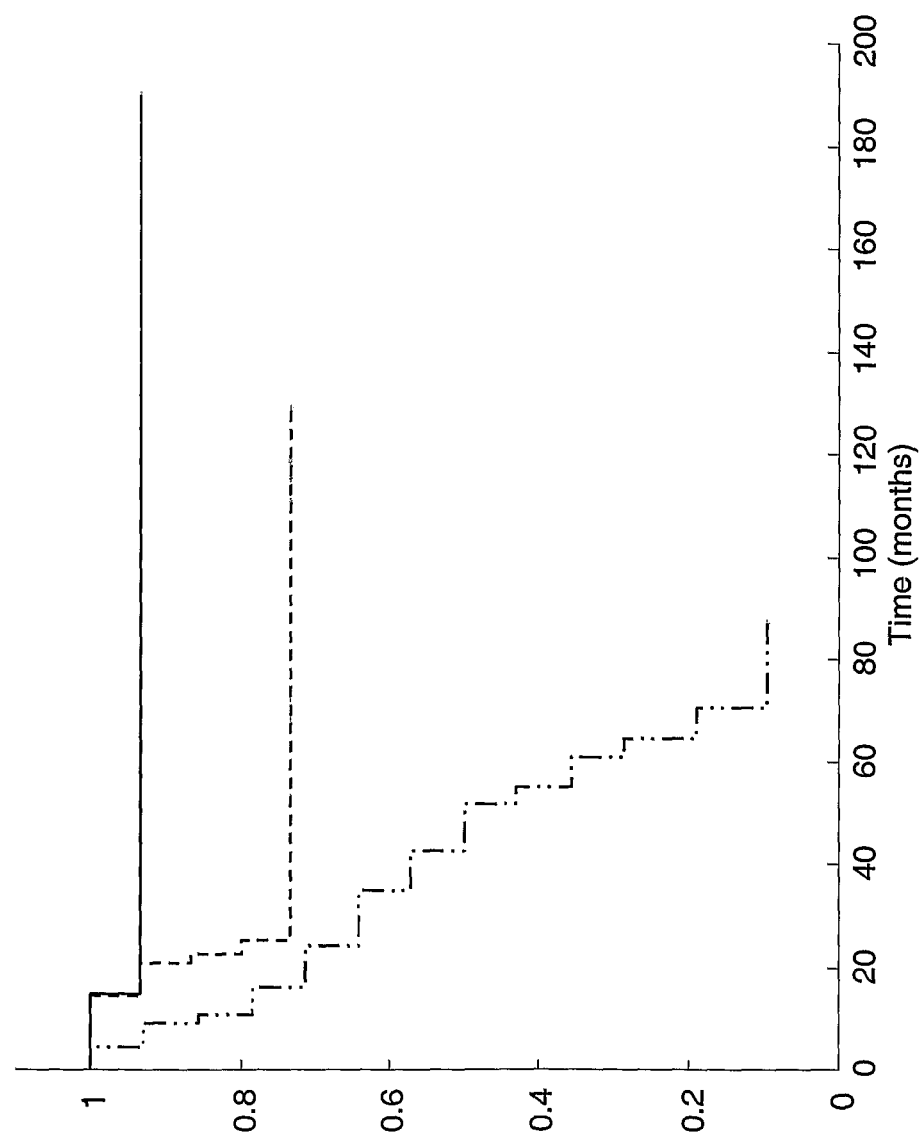
FIG. 8 is a Kaplan-Meier model of fractional survival for gastric cancer patients by time in months from surgery based on stage. P-value (6.2e-005) calculated by logrank between stages 1 and 3. Solid line—stage 1, n=15; dashed line—stage 2, n=15; dotted dashed line—stage 3, n=14.

Using the coefficients of the Cox fit for $\log_2$(miR reading), 0.683*expression, and 1.60*stage we created a composite variable with improved separation. The composite score is now used for separation, with lower values (corresponding to lower values of miR expression and lower stage) having better prognosis for survival. The separation, as demonstrated by logrank is excellent (FIG. 7), and much better than that for stage alone (FIG. 8).

Example 5

Predictive Value

The predictive value of the microRNA using logistic regression was maximized using the linear coefficients $b_0=-14.5826$ and $b_1=1.5975$ and the threshold 0.0756. This value allows for no false identification of non-recurrence within three years, while 14/31 of all non-recurring patients are correctly identified. The sensitivity for non-recurrence is thus 0.45 and the positive predictive value is 100% (95% CI: 73-100). This includes 5/7 in stage 3 and 5/11 in stage 2.

Example 6

Survival

Figure 9:
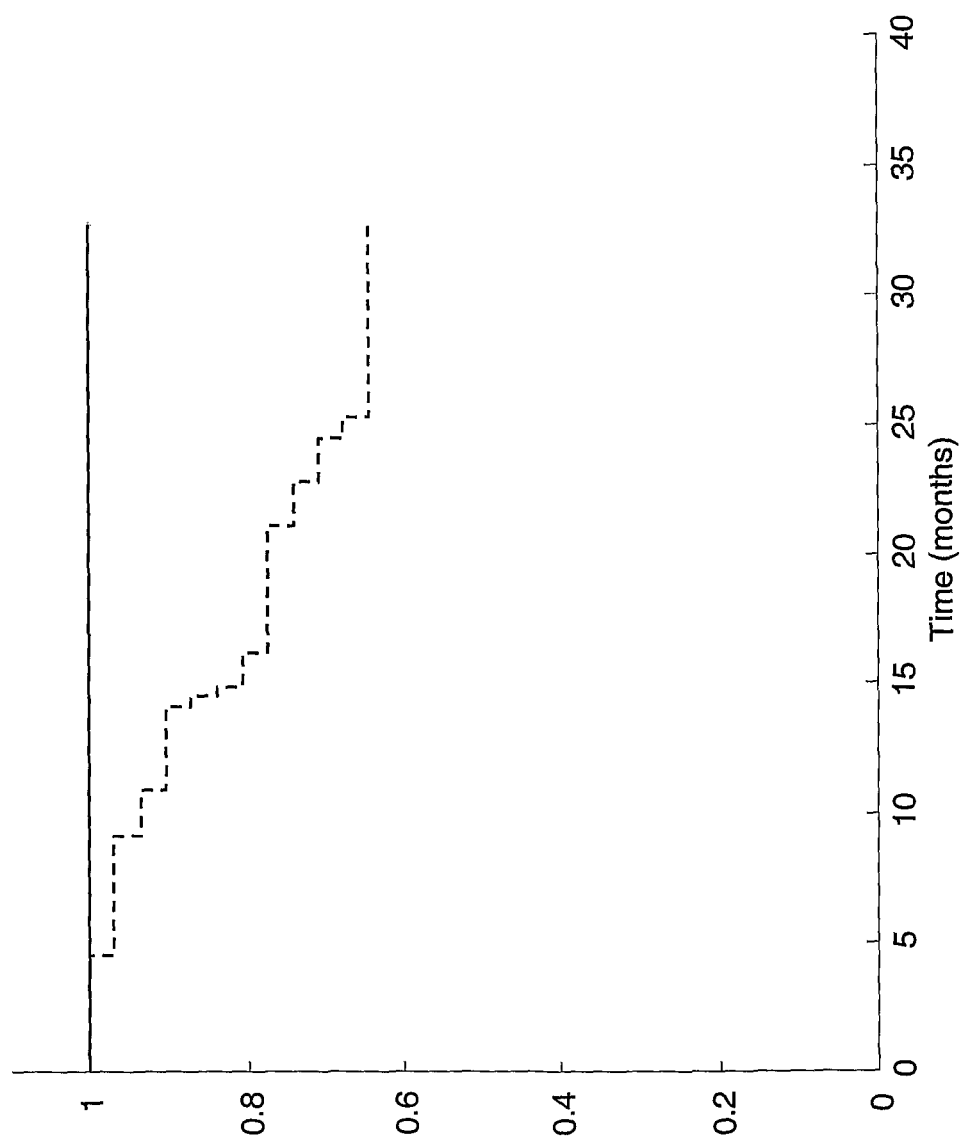
FIG. 9 is Kaplan-Meier model of fractional survival for gastric cancer patients by time in months from surgery based on log$_2$(hsa-miR-451 expression). Threshold maximizes separation. P-value (0.0083) calculated by logrank. Solid line—n=14 (≤0.075646), dashed line-n=31 (>0.075646).

Not only as regards prospects for recurrence is high hsa-miR-451 expression a bad omen. Splitting the population by median expression there is a clear separation with only 0/14 patients (0%) dying in the low-expression group as opposed to 11/31 (35%) in the high expression group (FIG. 9), thus suggesting a specificity for survival of 1 (95% CI: 0.68-1) and sensitivity of 0.41 (95% CI: 0.25-0.59).

The invention claimed is:

1. A method for determining a prognosis of gastric cancer in a human subject with gastric cancer, comprising:
   (a) obtaining a biological sample from the subject;
   (b) determining the expression level of SEQ ID NO: 1 in said sample by a nucleic acid hybridization method comprising contacting said sample with a probe, wherein the sequence of the probe consists of the complement of SEQ ID NO: 1, optionally attached to a linker sequence of 10-60 nucleotides, wherein the probe is attached to a solid substrate;
   (c) comparing said expression level to a reference threshold expression level; and
   (d) determining the prognosis of the gastric cancer based on the altered expression of SEQ ID NO: 1 in the sample relative to the reference threshold value, wherein increased expression of SEQ ID NO: 1 relative to the reference threshold is indicative of poor prognosis of gastric cancer in the subject.

2. The method of claim 1, wherein said biological sample is selected from the group consisting of bodily fluid, a cell line and a tissue sample.

3. The method of claim 2, wherein said tissue is a fresh, frozen, fixed, wax-embedded or formalin fixed paraffin-embedded (FFPE) tissue.

4. The method of claim 3, wherein said tissue is a gastric tissue.

5. The method of claim 4, wherein said gastric tissue is a tumor tissue at a specific stage.

6. The method of claim 1, wherein the sequence of the probe consists of the complement of SEQ ID NO: 1 attached to a linker sequence of 10-60 nucleotides.

* * * * *